US006468506B1

United States Patent

Rössling et al.

(10) Patent No.: US 6,468,506 B1
(45) Date of Patent: *Oct. 22, 2002

(54) PROCESS FOR PRODUCING POLYMERIC MICROPARTICLES, MICROPARTICLES PRODUCED BY SAID PROCESS AND THE USE OF SUCH PARTICLES IN MEDICAL DIAGNOSTICS

(75) Inventors: Georg Rössling; Celal Albayrak; Matthias Rothe, all of Berlin (DE)

(73) Assignee: Actipac Biosystems GmbH, Munich (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/913,312

(22) PCT Filed: Mar. 14, 1996

(86) PCT No.: PCT/EP96/00107

§ 371 (c)(1),
(2), (4) Date: Mar. 9, 1998

(87) PCT Pub. No.: WO96/28191

PCT Pub. Date: Sep. 19, 1996

(30) Foreign Application Priority Data

Mar. 14, 1995 (DE) ........................................ 195 10 690

(51) Int. Cl.[7] .............................. A61B 8/00; A61K 9/19

(52) U.S. Cl. ....................... 424/9.5; 424/9.52; 424/489; 424/450; 424/451; 424/455

(58) Field of Search ................................ 424/450, 451, 424/455, 9.52, 489, 9.5

(56) References Cited

U.S. PATENT DOCUMENTS

| | | | | |
|---|---|---|---|---|
| 5,043,280 A | * | 8/1991 | Fischer et al. | 435/235 |
| 5,425,366 A | * | 6/1995 | Reinhardt et al. | 128/662.02 |
| 5,558,854 A | * | 9/1996 | Quay | 424/9.52 |
| 5,711,933 A | * | 1/1998 | Bichon et al. | 424/9.52 |

FOREIGN PATENT DOCUMENTS

| | | |
|---|---|---|
| DE | 4 219 723 | 12/1993 |
| DE | 4 232 755 | 3/1994 |
| EP | 0 122 624 | 10/1984 |
| EP | 0 123 235 | 10/1984 |
| EP | 0 131 540 | 1/1985 |
| EP | 0 224 934 | 6/1987 |
| EP | 0 327 490 | 8/1989 |
| EP | 0 458 745 | 11/1991 |

OTHER PUBLICATIONS

Registry database (RN 308069–13–8, RN 308067–55–2), 2001.*

Bleich et al, International Journal of Pharmaceutics, 97 (1993) 111–117, 1993.*

R.A. Levine, “,” J. Am. Coll Cardiol., p. 28, (Dec. 19, 1998).

Roelandt et al., “,” Ultrasound Med. Biol, 8th ed., p. 471–492, (Dec. 19, 1982).

* cited by examiner

*Primary Examiner*—Diana Dudash
*Assistant Examiner*—Shahnam Sharareh
(74) *Attorney, Agent, or Firm*—Michael J. Rafa; Felissa H. Cugan

(57) ABSTRACT

The invention relates to a process for the production of gaseous microparticles for ultrasonic diagnosis, whose wall material is built up from polyesters of α-, β- or γ- hydroxycarboxylic acids, particles that are produced according to this process, as well as their use in medical diagnosis.

7 Claims, 1 Drawing Sheet

PROCESS FOR PRODUCING POLYMERIC MICROPARTICLES, MICROPARTICLES PRODUCED BY SAID PROCESS AND THE USE OF SUCH PARTICLES IN MEDICAL DIAGNOSTICS

The invention relates to the object that is characterized in the claims, i.e., a process for the production of gaseous microparticles for ultrasonic diagnosis, whose wall material is built up from polyesters of α-, β- or γ-hydroxycarboxylic acids, particles that can be produced according to this process, as well as their use in medical diagnosis.

Ultrasonic diagnosis has been used very extensively in medicine because of the trouble-free, simple handling. Ultrasonic waves are reflected at interfaces of different types of tissues. The echo signals that are produced in this case are electronically enhanced and made visible.

The visualization of blood vessels and internal organs using ultrasound generally does not allow the visualization of the blood flow that is present in it. Liquids, especially blood, yield ultrasonic contrast only if density and compressibility differences exist compared to the surrounding area. In medical ultrasonic diagnosis, e.g., substances that contain gases or that produce gas are used as contrast media since the impedance difference between gas and surrounding blood is considerably greater than that of liquids or solids and blood [Levine, R. A., J. Am. Coll. Cardiol. 3 (1989) 28; Machi, I. J. CU 11 (1983) 3].

Roelandt et al. [Ultrasound Med. Biol. 8 (1982) 471–492] describe that cardial echo contrasts can be achieved by peripheral injections of solutions that contain fine gas bubbles. These gas bubbles are created in physiologically compatible solutions by, e.g., shaking, other stirring or by addition of carbon dioxide. They are not standardized with respect to number or size, however, and can be reproduced only inadequately. Also, they are generally not stabilized, so that their service life is short. Their average diameters in most cases exceed that of an erythrocyte, so that it is not possible for them to pass through the pulmonary capillaries with subsequent contrasting of organs such as left heart, liver, kidney or spleen. Moreover, they are not suitable for quantification since the ultrasonic echo that they produce consists of several processes that cannot be separated from one another, such as bubble production, coalescence, and dissolution. Thus, it is not possible, e.g., with the aid of these ultrasonic contrast media to obtain information on transit times by measuring the history of the contrast in the myocardium. To this end, contrast media are needed whose scatter elements have sufficient stability.

EP 0 131 540 describes the stabilization of gas bubbles by sugar. This improves the reproducibility and homogeneity of the contrast effect, but these bubbles do not survive passing through the lungs.

EP 0 122 624 and 0 123 235 describe that the gas bubble-stabilizing effect of sugars, sugar alcohols, and salts is improved by the addition of surface-active substances. The passage through pulmonary capillaries and the possibility of visualizing the arterial femoral blood vessel and various organs such as the liver or spleen are provided for with these ultrasonic contrast media. In this case, however, the contrast effect is limited to the vascular lumen since the bubbles are not absorbed by the tissue cells.

None of the ultrasonic contrast media described remains unaltered in the body for a prolonged period of time. Organ visualization with sufficient signal intensity by selective concentration after i.v. administration or quantification is not possible with these agents.

Encapsulation of gases, such as, for example, air as ultrasonic contrast media is described in EP 0 224 934. The wall material that is used in this case consists of protein, especially human serum albumin with the known allergenic properties, which may also be accompanied by cytotoxic effects caused by denaturation.

Patent EP 0 327 490 describes gaseous microparticles for ultrasonic diagnosis based on biodegradable, synthetic materials. As biodegradable polymers, i.a., α-, β- or γ-hydroxycarboxylic acids are also disclosed. These agents have a sufficient in-vivo service life and, after intravenous administration, they concentrate intracellularly in the reticuloendothelial system and thus also in the liver or spleen, but the particles that are produced according to the examples of this application and that are based on hydroxycarboxylic acids have only a relatively small backscatter coefficient. The diagnostic action of contrast medium preparations that are prepared from them is therefore not satisfactory in all cases.

The object of this invention was therefore to provide an improved process for the production of microparticles based on polyesters of α-, β- or γ-hydroxycarboxylic acids, according to which it is possible to obtain particles that have a better backscatter coefficient than the particles of the prior art.

The particles and contrast medium preparations that are prepared from them should further meet the other requirements that are imposed on a modern contrast medium, such as, e.g., be small and stable enough to reach the left half of the heart after intravenous administration without significant gas loss and basically quantitative, to have good compatibility without having an allergenic potential, and not to agglomerate in an aqueous medium.

This object is achieved by this invention.

It has been found that microparticles based on polyesters can be produced from α-, β- or γ-hydroxycarboxylic acids, by the respective polyester and optionally a surface-active substance in an organic solvent or solvent mixture, of which at least one solvent is readily water-miscible, being dissolved, then a liquid perfluoro compound or water being dispersed in this solution, and then this dispersion being dispersed in water that contains a surface-active substance with the aid of a stirring mechanism, whereby the solvent is removed by pumping in gas and applying a vacuum. In this case, particles that contain first water or the liquid perfluoro compound precipitate out. Then, the suspension that contains particles is mixed with a suitable pharmaceutically acceptable cryoprotector and freeze-dried, whereby the liquid that is contained in the particles largely escapes, and is replaced after the freeze-drying device is aerated with the desired gas (generally air). Depending on the drying time, optionally a small amount of liquid (water or perfluoro compound) remains as vapor in the particles.

As a perfluoro compound, preferably perfluoropentane, perfluorohexane, perfluoro-1,3-dimethylcyclohexane, perfluorocyclohexene, perfluorodecalin, or perfluoroether is used.

Used as polymers in the process according to the invention are:

Polyglycolide (PGA), as well as its copolymers with L-lactide (PGA/PLLA) or polylactide (PLA), as well as its stereocopolymers such as, e.g., poly-L-lactide (PLLA), poly-DL-lactide or poly-L-lactide/DL-lactide or poly-β-hydroxybutyrate (PHBA), as well as its copolymers with β-hydroxyvalerate (PHBA/HVA) or poly-β-hydroxypropionate (PHPA) or poly-p-dioxanone (PDS) or poly-δ-valerolactone or poly-ξ-caprolactone.

In the copolymers between lactic acid (LA) and glycolic acid (GA), the molar ratio relative to the monomers is in the range of 85:15 to 50:50, preferably 75:25.

As organic solvents or solvent mixtures for the polymers, dichloromethane, acetone, ethyl acetate, methyl acetate, triacetin, triethyl citrate, ethyl lactate, isopropyl acetate, propyl formate, butyl formate, ethyl formate, and/or methyl lactate are preferably used.

As a surface-active substance (surfactant), substances from the group of Poloxamers(R) or Poloxamines(R), polyethylene glycol alkyl ethers, polysorbate, saccharose esters (Sisterna The Netherlands), saccharose esters [Ryoto sugar esters, (Tokyo)], gelatin, polyvinylpyrrolidone, fatty alcohol polyglycoside, Chaps (Serva), Chap (Calbiochem), Chapso (Calbiochem), decyl-β-D-glycopyranoside, decyl-β-D-maltopyranoside, dodecyl-β-D-maltopyranoside, sodium oleate, polyethylene glycol, polyvinyl alcohol or mixtures thereof are used.

As gases, air, nitrogen, oxygen, noble gases, dinitrogen oxide, carbon dioxide, halogenated hydrocarbons, saturated or unsaturated hydrocarbons in gaseous form, nitrogen dioxide, and/or ammonia are used.

An alternative process for the production of microparticles based on polyesters of α-, β- or γ-hydroxycarboxylic acids consists in the desired polymer(s) and optionally an amino acid being dissolved in at least one organic solvent and this solution being sprayed via a nozzle into a column that is filled with a supercritical gas or through which the latter flows, whereby the solvent is taken up by the supercritical gas.

As polymers or copolymers, the same substances as were mentioned in the first-mentioned production process are used in this process variant. The equivalent applies for the mixing ratios in the copolymers. Preferably, an amino acid is provided instead of the surfactant in the dissolved polymers (polyesters) that are used in each case. As amino acids, preferably L-lysine, L-phenylalanine, L-tryptophan, as well as D,L-phenylalanine are used.

As solvents or solvent mixtures, the solvents that are cited in the first process variant are suitable.

The addition of a perfluoro compound is not necessary in this case.

As supercritical gases, dinitrogen oxide, carbon dioxide, halogenated hydrocarbons, saturated or unsaturated hydrocarbons, nitrogen dioxide, and/or ammonia are used, wherein carbon dioxide is preferred. The supercritical gases can optionally contain up to 10% additives such as, e.g., lower alcohols, such as, e.g., ethanols, esters, or gases, such as, e.g., nitrogen.

The size of the resulting particles can be controlled by type, size and shape of the injection nozzle, working pressure and temperature in the column. A particle size as is necessary for an intravenously administered ultrasonic contrast medium (<10 $\mu$m) can be obtained by using a nozzle with a nozzle diameter of 0.5 mm and a spraying angle of 10° at a working pressure of between 90 and 100 bar, preferably 94–96 bar and a temperature of 36° C.

Another aspect of the invention relates to microparticles for ultrasonic diagnosis that can be produced according to the above-named process.

Another aspect of the invention relates to contrast media for ultrasonic diagnosis that contain microparticles, which were produced according to the above-mentioned process.

These agents can be obtained by the dried microparticles being resuspended in a pharmaceutically acceptable suspension medium.

As pharmaceutically acceptable suspension media, for example, water p.i., aqueous solutions of one or more inorganic salts, such as physiological electrolyte solutions and buffer solutions, such as, e.g., Tyrode's solution, aqueous solutions of mono- or disaccharides such as glucose or lactose, sugar alcohols such as mannitol, which optionally in addition have a surface-active substance, e.g., from the group of polysorbates or polysaccharides, polyvinylpyrrolidone, polyethylene glycol, saccharose mono- and diesters or substances from the group of poloxamers or poloxamines or their mixtures and/or a physiologically compatible multivalent alcohol such as glycerine are suitable. Preferred is, however, water that is suitable for injection purposes.

To increase the reliability of administration, the suspension can be filtered immediately before injection.

The microparticles that are produced according to the process of the invention that are based on polyesters of α-, β- or γ-hydroxycarboxylic acids or contrast media that are prepared from them meet all requirements that are set on an ultrasonic contrast medium. The particles that are contained in the agents are distinguished by the following advantages:

- They are quickly degraded in vivo,
- degradation products are toxicologically harmless,
- they circulate for a sufficiently long period in the blood circulation,
- they can be used in all modes of ultrasonic diagnosis, especially also in modes in which nonlinear effects are used,
- they are well-tolerated,
- they have a uniform, controllable size distribution,
- they are easy to produce,
- the polymeric particles have a narrow molecular weight distribution,
- they are sufficiently stable to survive passing through the lungs and thus are also suitable for contrasting the left heart, and
- they are taken up by the reticuloendothelial system and thus are also suitable for contrasting the liver and spleen.

The particles that are produced according to the process of the invention especially have a larger backscatter coefficient than the particles that are disclosed in EP 0 327 490 which also are built up from α-, β-, γ-hydroxycarboxylic acids. This was also shown in a comparison test. Thus, for a freshly prepared suspension of the particles in water described in EP 0 327 490 (Example 1) (concentration 18.6 mg/ml) after 5 minutes, a backscatter coefficient of $\alpha_s=4\times10^{-4}$ [Db/cm] at 5 MHz of transmitter frequency was measured, while for a preparation according to the invention (particles according to Example 1 suspended in water/concentration 0.18 mg/ml) under otherwise identical conditions, a backscatter coefficient of as $\alpha_s=2.7\times10^{-1}$ [dB/cm] was measured. It is taken into consideration that the concentration of the preparations according to the invention was smaller by a factor 100 than the comparison preparation, i.e., an increase of the backscatter coefficients by five orders of magnitude results. Since the imaging effect depends directly on the backscatter coefficient, the particles that are produced according to the invention represent considerably more effective contrast media.

The determination of the backscatter coefficient is done in an in-vivo experimental set-up, in which the backscattered signal caused by a contrast medium that is present in a vessel is measured (see also "Standardization of the Measurement of Acoustical Parameters of Ultrasound Contrast Agents" First European Symposium on Ultrasound Contrast Imaging, Jan. 25–26, 1996, Rotterdam).

The examples below are used for a more detailed explanation of the object of the invention, without intending that it be limited to these examples.

EXAMPLE 1

Figure 1:
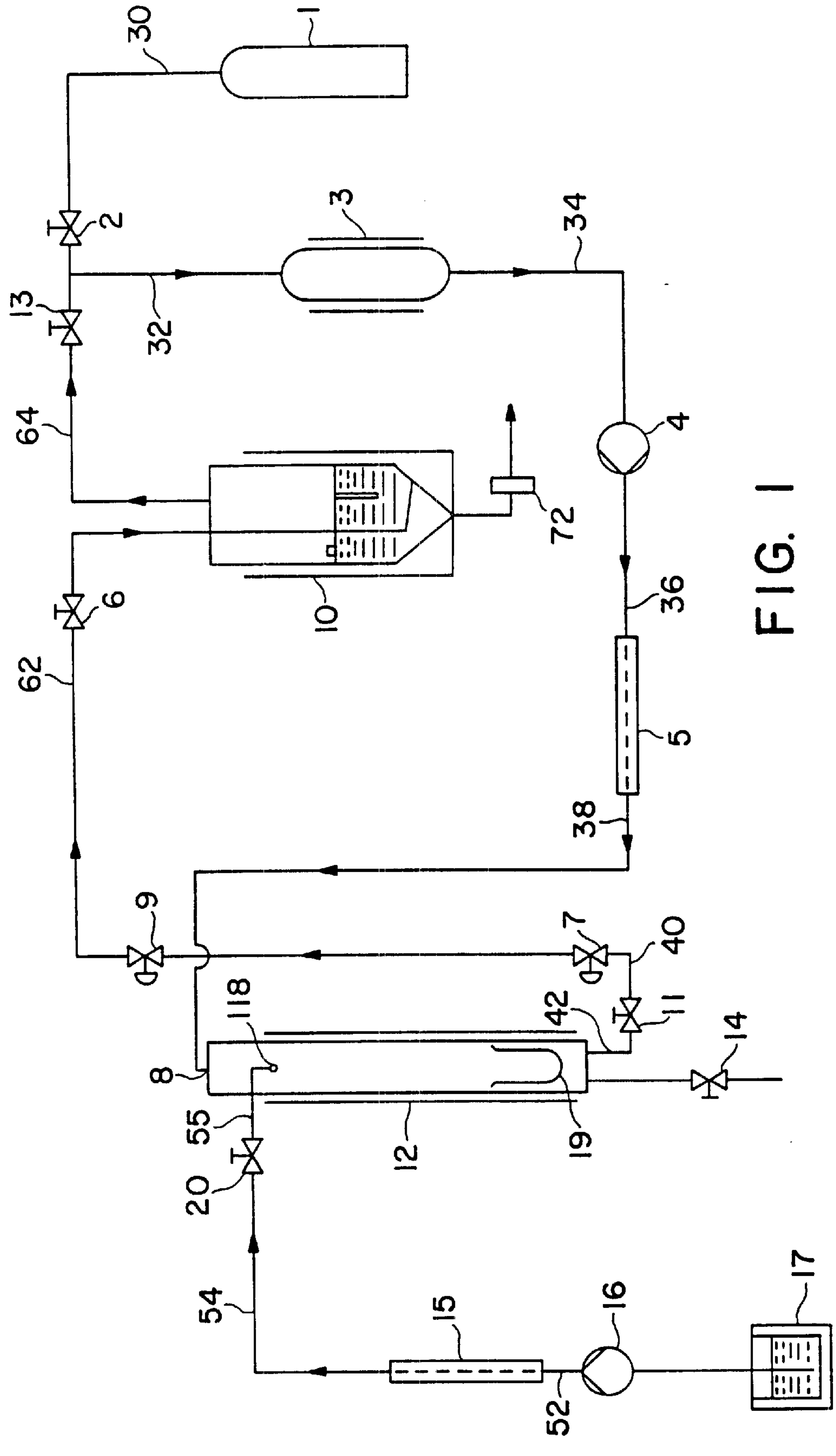
FIG. 1 is a diagram of an apparatus in accordance with one embodiment of the invention, as further described in Example 34 below. Solutions of the polyester and of the amino acid are combined to form a polyester solution and are added to tank (17). The unit is filled with gas via valve (2) and line (30), from storage bottle (1). With reciprocating pump (16), the polyester solution is fed from tank (17) to nozzle (118), after flowing through line (52), heat exchanger (15), line (54), valve (20), and line (55). The polyester solution is sprayed into column (12) by nozzle (118), and $CO_2$ in a supercritical state is directed through the column in parallel flow via intake (8). Gas charged with solvent flows out the end of the column through lines (42) and (40), controlled by magnet valves (7 and 9). The gas charged with solvent is directed by line (62) into separator (10) that is temperature-equalized to 21 ° C., where $CO_2$ separates from the solvent mixture. The $CO_2$ is then brought back into the supercritical state using lines (64) and (32), by raising the pressure (3) and temperature (4). The recycled $CO_2$ is fed to the column via line (34), liquid gas pump (4), line (36), heat exchanger (5), and line (38), via intake (8). Solvent mixture that is separated in separator (10) is removed after separator (10) is shut-off from the circuit by valves (6) and (13), and after depressurization of the separator to atmospheric pressure via valve (72). At the end of the drying process, the $CO_2$ flow to the column is shut-off and the column above valves (11) and (14) is depressurized to atomospheric pressure, and the particles are removed at the lower column end of the column (19).

3 g of polymer Resomer$^{(R)}$ RG-502 (Böhringer Ingelheim) is dissolved in 40 ml of methylene chloride/acetone (volume proportion 50:50). 10 ml of perfluoropentane is dispersed using Ultraturrax (10,000 rpm) for 2 minutes in the polymer solution. The emulsion that is produced (O/O) is dispersed in 400 ml of 1% gelatin solution, which is temperature-equalized to 0° C., using a mechanical stirring mechanism (Dispermat-FT, VMA-Getzmann GmbH), (1000 rpm) for 30 minutes. The emulsion (O/O/W) is moved into a 2 1 three-necked flask that is equipped with a stirring mechanism (300 rpm), and the solvent is removed for 3 hours at 20° C. by pumping in $N_2$ and for 3 hours at 25° C. by vacuum. Then, the suspension is mixed with a cryoprotector and freeze-dried.

The lyophilizate that is resuspended with water contains microparticles (diameter 0.2–8 $\mu$m) and has an excellent in-vitro backscatter coefficient [$\alpha_s$=2.7×10$^{-1}$ [dB/cm] at 5 mHz transmitter frequency and a particle number of C32 4×10$^6$]. The determination of the particle diameter was done on an LS-130 of the Coulter Electronics GmbH company, which executes a combination of light scattering and Fraunhofer diffraction. The determination of particle number was done with a Coulter Counter.

EXAMPLE 2

The procedure is as in Example 1, whereby perfluoropentane is replaced with perfluorodecalin. The lyophilizate that is resuspended with water contains ultrasound-active microparticles with a diameter of 0.2 to 8 $\mu$m.

EXAMPLE 3

The procedure is as in Example 1, whereby perfluoropentane is replaced by perfluorohexane. The lyophilizate that is resuspended with 0.9% NaCl solution contains ultrasound-active microparticles with a diameter of 0.2 to 8 $\mu$m.

EXAMPLE 4

The procedure is as in Example 1, whereby perfluoropentane is replaced by perfluoro-1,3-dimethylcyclohexane.

The lyophilizate that is resuspended with 5% mannitol solution contains ultrasound-active microparticles with a diameter of 0.2 to 8 $\mu$m.

EXAMPLE 5

The procedure is as in Example 1, whereby perfluoropentane is replaced by perfluoroheptane. The lyophilizate that is resuspended with 5% mannitol solution contains ultrasound-active microparticles with a diameter of 0.2 to 8 $\mu$m.

EXAMPLE 6

The procedure is as in Example 1, whereby the polymer Resomer$^{(R)}$ RG-502 is replaced by Resomer$^{(R)}$ RG-503. The lyophilizate that is resuspended with 0.9% NaCl solution contains ultrasound-active microparticles with a diameter of 0.2 to 8 $\mu$m.

EXAMPLE 7

The procedure is as in Example 1, whereby the polymer Resomer$^{(R)}$ RG-502 is replaced by Resomer$^{(R)}$ RG-504 and is dissolved in 45 ml of methyl chloride/acetone (volume proportion 55:45). The lyophilizate that is taken up with 0.9% NaCl solution contains ultrasound-active microparticles with a diameter of 0.2 to 8 $\mu$m.

EXAMPLE 8

The procedure is as in Example 1, whereby the polymer Resomer$^{(R)}$ RG-502 is replaced by Resomer$^{(R)}$ RG-756 and is dissolved in 50 ml of methyl chloride/acetone (volume proportion 60:40). The lyophilizate that is resuspended with water contains ultrasound-active microparticles with a diameter of 0.2 to 8 $\mu$m.

EXAMPLE 9

The procedure is as in Example 1, whereby the polymer Resomer$^{(R)}$ RG-502 is replaced by Resomer$^{(R)}$ RG-858 and is dissolved in 65 ml of methyl chloride/acetone (volume proportion 63:37). The lyophilizate that is resuspended with water contains ultrasound-active microparticles with a diameter of 0.2 to 8 $\mu$m.

EXAMPLE 10

The procedure is as in Example 1, whereby perfluoropentane is replaced by perfluorohexane and the polymer Resomer$^{(R)}$ RG-502 is replaced by Resomer$^{(R)}$ RG-858 and is dissolved in 65 ml of methylene chloride/acetone (volume proportion 63:37). The lyophilizate that is taken up with water contains ultrasound-active microparticles with a diameter of 0.2 to 8 $\mu$m.

EXAMPLE 11

The procedure is as in Example 1, whereby perfluoropentane is replaced by perfluorodecalin and the polymer Resomer$^{(R)}$ RG-502 is replaced by Resomer$^{(R)}$ RG-858 and is dissolved in 65 ml of methylene chloride/acetone (volume proportion 63:37). The lyophilizate that is taken up with water contains ultrasound-active microparticles with a diameter of 0.2 to 8 μm.

EXAMPLE 12

The procedure is as in Example 1, whereby the polymer Resomer(R) RG-502 is replaced by Resomer(R) R-208. The lyophilizate that is resuspended with water contains ultrasound-active microparticles with a diameter of 0.2 to 8 μm.

EXAMPLE 13

The procedure is as in Example 1, whereby acetone is replaced by ethyl acetate. The lyophilizate that is taken up with water contains ultrasound-active microparticles with a diameter of 0.2 to 8 μm.

EXAMPLE 14

The procedure is as in Example 1, whereby the acetone is replaced by methyl acetate. The lyophilizate that is resuspended with water contains ultrasound-active microparticles with a diameter of 0.2 to 8 μm.

EXAMPLE 15

The procedure is as described in Example 1, whereby the polymer Resomer(R) RG-502 is replaced by Resomer(R) RG-858, and acetone is replaced by ethyl acetate. The lyophilizate that is resuspended with water contains ultrasound-active microparticles with a diameter of 0.2–8 μm.

EXAMPLE 16

The procedure is as described in Example 1, whereby the perfluoropentane is replaced by 10 ml of 20% glucose solution. The lyophilizate that is resuspended with water contains ultrasound-active microparticles with a diameter of 0.2 to 8 μm.

EXAMPLE 17

The procedure is as described in Example 1, whereby instead of 3 g, only 2 g of polymer Resomer(R) RG-502 is used. The lyophilizate that is taken up with 5% mannitol solution contains ultrasound-active microparticles with a diameter of 0.1 to 8 μm.

EXAMPLE 18

The procedure is as in Example 1, whereby the polymer Resomer(R) RG-502 is replaced by 1 g of PHB/PHN copolymer (12% PHV, biopol ICI), gelatin solution with 200 ml of a 1% PVA solution (MW 9–10×$10^3$ dalton), and the polymer is dissolved in 30 ml of methylene chloride/acetone (volume proportion 66:34).

The lyophilizate that is resuspended with water contains ultrasound-active microparticles with a diameter of 0.4 to 8 μm.

EXAMPLE 19

The procedure is as in Example 1, whereby the polymer Resomer(R) RG 502 is dissolved with 1 g of a PHB/PVB copolymer (18% PHV, biopol ICI), gelatin solution with 200 ml of a 1% PVA solution in 30 ml of methylene chloride/acetone (volume proportion 66:34). The lyophilizate that is resuspended with water contains ultrasound-active microparticles with a diameter of 0.4 to 8 μm.

EXAMPLE 20

The procedure is as in Example 1, whereby the polymer Resomer(R) RG 502 is replaced by 1 g of polycaprolactomes [inherent vis: 1.26 dl/g in $CHCl_3$ at 30° C. (Birmingham Polymers NC, US], gelatin is replaced by 200 ml of a 1% PVA solution (MW 9–10 kDal), and the polymer is dissolved in 30 ml of methylene chloride/acetone (volume proportion 70:30). The lyophilizate that is resuspended with water contains ultrasound-active microparticles with a diameter of 0.2 to 8 μm.

EXAMPLE 21

The procedure is as in Example 1, whereby gelatin is replaced by 400 ml of 3% Pluronic(R) F. 68 solution. The lyophilizate that is resuspended with 5% mannitol solution contains ultrasound-active microparticles with a diameter of 0.4 to 8 μm.

EXAMPLE 22

The procedure is as in Example 1, whereby gelatin is replaced by 400 ml of a 0.5% Na-oleate solution.

The lyophilizate that is taken up with 5% mannitol solution contains ultrasound-active microparticles with a diameter of 0.5 to 8 μm.

EXAMPLE 23

The procedure is as in Example 1, whereby gelatin is replaced by 400 ml of a 1% octyl-β-D-glucopyranoside solution.

The lyophilizate that is resuspended with water contains ultrasound-active microparticles with a diameter of 0.1 to 8 μm.

EXAMPLE 24

The procedure is as in Example 1, whereby gelatin solution is mixed by 400 ml of 1% saccharose palmitate P-1570 (Ryoto Sugar esters).

The lyophilizate that is resuspended with water contains ultrasound-active microparticles with a diameter of 0.1 to 7 μm.

EXAMPLE 25

The procedure is as in Example 1, whereby gelatin solution is replaced by 400 ml of 1% saccharose stearate (Ryoto sugar esters) S-1670.

The lyophilizate that is resuspended with water contains ultrasound-active microparticles with a diameter of 0.1 to 7 μm.

EXAMPLE 26

The procedure is as in Example 1, whereby instead of gelatin solution, 400 ml of 1% saccharose diester, SP 70 (Sisternen, the Netherlands) is used.

The lyophilizate that is resuspended with water contains ultrasound-active microparticles with a diameter of 0.1 to 7 μm.

EXAMPLE 27

The procedure is as in Example 1, whereby methylene chloride/acetone solution mixture is replaced by 70 ml of ethyl acetate and 18 ml of perfluoropentane is used instead of 10 ml of perfluoropentane.

The lyophilizate that is resuspended with water contains ultrasound-active microparticles with a diameter of 0.1 to 5 μm.

EXAMPLE 28

The procedure is as in Example 1, whereby acetone is replaced by ethyl acetate. The lyophilizate that is taken up with water contains ultrasound-active microparticles with a diameter of 0.1 to 7 μm.

EXAMPLE 29

The procedure is as in Example 1, whereby acetone is replaced by methyl acetate. The lyophilizate that is resuspended with water contains ultrasound-active microparticles with a diameter of 1 to 7 μm.

EXAMPLE 30

The procedure is as in Example 1, whereby acetone is replaced by methyl acetate. The lyophilizate that is resuspended with water contains ultrasound-active microparticles with a diameter of 1 to 6 μm.

EXAMPLE 31

The procedure is as in Example 1, whereby acetone is replaced by ethyl acetate. The lyophilizate that is taken up with water contains ultrasound-active microparticles with a diameter of 0.1 to 6 μm.

EXAMPLE 32

The procedure is as in Example 1, whereby acetone is replaced by triacetin. The lyophilizate that is resuspended with water contains ultrasound-active microparticles with a diameter of 1 to 7 μm.

EXAMPLE 33

The procedure is as in Example 1, whereby acetone is replaced by triethyl citrate. The lyophilizate that is resuspended with water contains ultrasound-active microparticles with a diameter of 1 to 7 μm.

EXAMPLE 34

0.375 g of L-lysine (Aldrich) is dissolved in 25 ml of glacial acetic acid (Merck); 2.5 g of Resomer(R) RG-756 (B öhringer Ingelheim) is dissolved in 75 ml of dichloromethane (Merck). The combined solutions are further treated in an apparatus as pictured in FIG. 1.

The combined solutions are first added to a tank (17), and the unit is filled with gas via valve (2) and line (30) from a storage bottle. Using a reciprocating pump (16), the solution is fed to nozzle (118) from tank (17) after flowing through line (52) to a heat exchanger (15), a line (54), a valve (20) and finally line (55). At a pressure of 94–96 bar, the solution that contains the copolymer is sprayed into column (12) by a conventional one-component nozzle (118) [Schlick 121 V type], whereby simultaneously $CO_2$ in a supercritical state is directed through the column with 90 bar/36° C. and a throughput of 8.9 kg/h in parallel flow, via intake (8). The nozzle has a diameter of 0.5 mm, and the spraying angle is 10°.

Corresponding to the high affinity of the supercritical $CO_2$ for the solvent, solvent is removed from the primarily formed droplets. Spherical solid polymer particles remain.

The additional steps are used basically to purify and recycle the solvent-charged $CO_2$, but no longer have anything to do with the production of particles. The working-up of the $CO_2$ can be done as follows. The gas that is charged with solvent flows out the end of the column through lines (42) and (40), controlled by 2 magnet valves (7 and 9), and is expanded to 60 bar. The valves are switched in such a way that the quantity of liquid gas that flows into the column per unit of time can flow in while maintaining the working pressure of the column. The $CO_2$, which is cooled by expansion to 60 bar and charged with solvent, is directed by line (62) into separator (10) that is temperature-equalized to 21° C., where the solvent mixture separates into $CO_2$ because of the strongly reduced solubilities under these conditions. The $CO_2$ from which the solvent mixture is removed is brought back into the supercritical state (90 bar, 36° C.) using lines (64 and 32) by raising the pressure and temperature (3 and 4), and to further dry the particles that are produced it is again fed to the column via line (34), liquid gas pump (4), line (36), heat exchanger (5), line (38) via intake (8).

The removal of the solvent mixture that is separated in separator (10) is done after separator (10) is separated from the circuit by valves (6) and (13) and after depressurization to atmospheric pressure is done via valve (72).

After the entire quantity of dissolved polymer contained in the reservoir has been sprayed (time period, depending on pressure, 20 to 50 minutes), $CO_2$ is run through the column until solvent radicals can no longer be recovered in separator (10).

After the drying process has ended, the $CO_2$ flow to the column is shut off, the column above valves (11) and (14) is depressurized to atmospheric pressure, and the particles are removed at lower column end (19).

Ultrasound-active, gaseous microparticles with a diameter of 5–10 μm are obtained.

EXAMPLE 35

0.375 g of L-lysine (Aldrich), 2.5 g of polymer (RG-756) are dissolved in 25 ml of glacial acetic acid. (Merck) and 75 ml of dichloromethane (Merck) and stirred until a clear solution is produced. The rest of the reaction is carried out analogously to Example 34.

Ultrasound-active, gaseous microparticles with a diameter of 5–10 μm are obtained.

EXAMPLES 36–41

The production of further microparticles is done analogously to Example 34. The polymers that are used in each case as well as additional data are summarized in Table 1.

In all cases, ultrasound-active, gaseous microparticles are obtained. The ultrasound-active, hollow microparticles that are obtained are sterile and free of solvent residue, polymerization catalysts or initiator molecules. They have a uniform particle size distribution of 5 to 10 μm.

The polymers are dissolved in each case in 75 ml of dichloromethane (Merck) and 25 ml of glacial acetic acid, and the respective quantity of amino acid is added. D,L-Phenylalanine is suitably to be dissolved in advance in up to 50 ml of methanol (Merck).

TABLE 1

| Test Number | Polymer or Copolymer | Weighed Portion of Polymer [g] | Amino Acid | Weighed Portion of Amino Acid [g] | Molar Ratio of Lactide/ Glycolide |
|---|---|---|---|---|---|
| 36 | Poly-(D,L)-lactide | 2.0 | L-lysine | 0.5 | |
| 37 | Poly-(D,L)-lactide-coglycolide | 1.0 | L-phenyl-alanine | 0.25 | 75:25 |
| 38 | Poly-(D,L)-lactide-coglycolide | 2.0 | D,L-phenyl-alanine | 0.5 | 75.25 |
| 39 | Poly-(D,L)-lactide-coglycolide | 2.2 | L-trypto-phan | 0.55 | 75:25 |
| 40 | Poly-L-lactide | 6.0 | L-lysine | 0.9 | |
| 41 | Poly-L-lactide | 3.0 | L-lysine | 0.45 | |

What is claimed is:

1. A process for the production of gaseous microparticles for ultrasonic diagnosis, whose wall material is built up from polyesters of α-, β-, or γ-hydroxycarboxylic acids, comprising:

dissolving the polyester(s) and optionally a surface-active substance in an organic solvent or solvent mixture to obtain a polyester solution, of which at least one solvent is readily water-miscible, dispersing a liquid perfluorinated compound which is not a solvent for the polymer in the polyester solution to obtain a dispersion and then dispersing the dispersion in water that contains a surface-active substance using a stirring mechanism, removing the solvent by pumping in gas and applying a vacuum to obtain a suspension, and mixing the suspension with a suitable pharmaceutically acceptable cryoprotector and freeze-drying to yield gaseous microparticles.

2. The process according to claim 1 wherein the wall material consists of a polymer selected from the group consisting of polyglycolide (PGA), its copolymers with L-lactide (PGA/PLLA), polylactide (PLA), its stereocopolymers, poly-β-hydroxbutyrate (PHBA), its copolymers with β-hydroxyvalerate (PHBA/HVA), poly-β-hydroxypropionate (PHPA), poly-p-dioxanone (PDS), poly-δ-valerolactone or poly-ξ-carprolactone.

3. The process according to claim 2, wherein for copolymers from lactic acid and glycolic acid, the ratio of lactic acid to glycolic acid is in the range of 85:15 to 50:50.

4. The process according to claim 1, wherein at least one organic solvent is selected from the group consisting of dichloromethane, acetone, ethyl acetate, methyl acetate, triacetin, triethyl citrate, ethyl lactate, isopropyl acetate, propyl formate, butyl formate, ethyl formate or ethyl lactate.

5. The process according to claim 1, wherein the perfluorinated compound is selected from the group consisting of, perfluoropentane, perfluorohexane, perfluoro-1,3-dimethylcyclohexane, perfluorocyclohexene, perfluorodecalin, and perfluoroether.

6. The process according to claim 1, wherein the surface-active substance is selected from the group consisting of poloxamers, poloxamines, polyethylene glycol alkyl ethers, polysorbates, saccharose esters, saccharose-esters, gelatin, polyvinylpyrrolidone, fatty alcohol polyglycoside, chaps, chap, chapso, decyl- -D-glycopyranoside, decyl- -D-maltopyranoside, dodecyl- -D-maltopyranoside, sodium oleate, polyethylene glycol, polyvinyl alcohol, or mixtures thereof.

7. The process according to claim 2, wherein the stereocopolymer is selected from the group consisting of poly-L-lactide (PLLA), poly-DL-lactide, or L-lactide/DL-lactide.

* * * * *